United States Patent [19]

Bartolo

[11] 4,428,364

[45] Jan. 31, 1984

[54] SELF-SEALING INJECTION BUTTON AND METHOD OF MAKING SAME

[75] Inventor: Anthony J. Bartolo, Midland, Mich.

[73] Assignee: Dow Corning Corporation, Midland, Mich.

[21] Appl. No.: 399,071

[22] Filed: Jul. 16, 1982

Related U.S. Application Data

[63] Continuation of Ser. No. 28,946, Apr. 11, 1979, abandoned.

[51] Int. Cl.$^3$ .............................................. A61B 19/00
[52] U.S. Cl. ........................................... 128/1 R; 3/1; 3/36
[58] Field of Search ...... 128/1 R, DIG. 21, DIG. 25, 128/346; 3/36

[56] References Cited

U.S. PATENT DOCUMENTS

| | | | |
|---|---|---|---|
| 3,402,710 | 9/1968 | Paleschuck | 128/1 |
| 3,600,718 | 8/1971 | Boone | 3/36 |
| 3,831,583 | 8/1974 | Edmunds et al. | 128/1 R |
| 3,919,724 | 11/1975 | Sanders et al. | 3/36 |
| 3,971,376 | 7/1976 | Wichterle | 128/260 |
| 4,019,499 | 4/1977 | Fitzgerald | 128/1 R |
| 4,138,382 | 2/1979 | Polmanteer | 260/29.6 TA |
| 4,184,489 | 1/1980 | Burd | 128/214 R |

FOREIGN PATENT DOCUMENTS

| | | |
|---|---|---|
| 1271812 | 4/1972 | United Kingdom . |
| 1316323 | 5/1973 | United Kingdom . |
| 1484539 | 9/1977 | United Kingdom . |

OTHER PUBLICATIONS

Data Sheet Entitled "Fluid Resistance of Silastic ® Brand Silicone Rubber", Dow Corning Corporation, Form No. 09-177 (1967).

Primary Examiner—John D. Yasko
Attorney, Agent, or Firm—Richard E. Rakoczy

[57] ABSTRACT

There is described a self-sealing injection button adapted to be punctured by a hypodermic needle and a method for making such device. The button is preferably a unitary composite comprising at least one sheet of cloth or metal fabric impregnated with cured silicone rubber which has been swollen by absorption of a nonvolatile swelling agent such as dimethylpolysiloxane fluid. An alternate embodiment restrains the rubber in a rigid ring shaped retainer. The preferred method of making the device comprises interleaving the fabric sheets with uncured silicone rubber sheets, compressing the composite to embed the fabric in the uncured rubber, curing the rubber, and then immersing the cured composite in the swelling agent.

9 Claims, 6 Drawing Figures

SELF-SEALING INJECTION BUTTON AND METHOD OF MAKING SAME

This application is a continuation of U.S. Ser. No. 28,946, filed Apr. 11, 1979, now abandoned.

BACKGROUND OF THE INVENTION

The present invention relates to self-sealing injection buttons for medical devices such as inflatable devices which are designed to be implanted in the body and then inflated in situ by introduction of a hypodermic needle or the like. Such injection buttons are also usable in permanently or semipermanently implanted devices for drug administration.

For example, Edmunds et al, U.S. Pat. No. 3,831,583 shows an implantable bulb designed for use with a blood vessel constricting device. In this prior art device, the injection button comprises a silicone gel filled elastomeric bulb adapted to be pierced by a hypodermic needle for introduction of an inflating fluid. Upon withdrawal of the needle the gel flows to seal the puncture hole.

While such devices are functional they are relatively expensive to manufacture and there is at least some small danger of the gel being forced from the bulb in the event of extreme pressure within the device, especially if a tear should propagate in the thin rubber shell due to piercing.

Other devices designed for similar purposes exist in the prior art and include gels, thick soft rubber sections or valves designed for introduction of a tubular device for introduction or withdrawal of liquid materials. Such devices are designed to be used on inflatable mammary prostheses, blood vessel restricters, and drug injection systems, for example. A need continues to exist, however, for an economical device which offers more positive sealing after puncture.

SUMMARY OF THE INVENTION

It is the primary object of the present invention to provide an improved self-sealing injection button which provides positive sealing and is more economical to manufacture than prior art devices designed for similar purposes and to provide a method for making such devices.

In accordance with a preferred embodiment, the present invention comprises a unitary composite body of at least one sheet of cloth or metal mesh fabric impregnated with cured silicone rubber swollen with a swelling agent for the rubber to provide compressive forces therein for sealing punctures made by a hypodermic needle or the like. The preferred embodiment of the method of manufacturing the device comprises interleaving alternate sheets of uncured silicone rubber with multiple sheets of cloth fabric, subjecting the composite so formed to pressure to embed the fabric in the raw silicone rubber, then curing the silicone rubber and, after curing, swelling the cured rubber by immersing it in a swelling agent such as dimethylpolysiloxane fluid. If the fabric weave is such that the material is stretchable in one direction it is necessary that the fabric sheets be rotated relative to one another in the interleaving process so that relatively rigid restraints against fabric stretching are provided. Alternatively, restraining means other than cloth fabric may be utilized for the rubber. Alternative embodiments of the invention include use of a metal mesh fabric in place of the cloth, use of a single sheet of relatively thick cloth and use of a rigid retaining ring to confine the rubber as it is swollen.

The swelling of the rubber in the composite combined with the restraint provided by the relative rigidity of the fabric or by the ring shaped retaining means thereby provides internal compressive forces distributed in the rubber which act immediately to seal punctures caused by hypodermic needles or the like upon withdrawal, providing positive sealing. The fabric serves also to restrain any tendency toward tear progagation. Fabrication is a relatively simple process compared with processes required, for example, to fabricate gel filled buttons such as those of the aforementioned Edmunds et al patent. Labor therefore is minimized and materal costs are relatively low.

BRIEF DESCRIPTION OF DRAWINGS

The invention will become better understood by reference to the accompanying drawings wherein.

DESCRIPTION OF PREFERRED EMBODIMENTS

Figure 1:
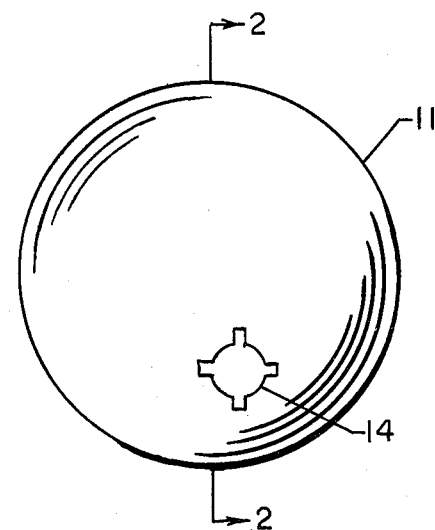
FIG. 1 is a front view in elevation of an inflatable mammary prosthesis made in accordance with the present invention.
Figure 2:
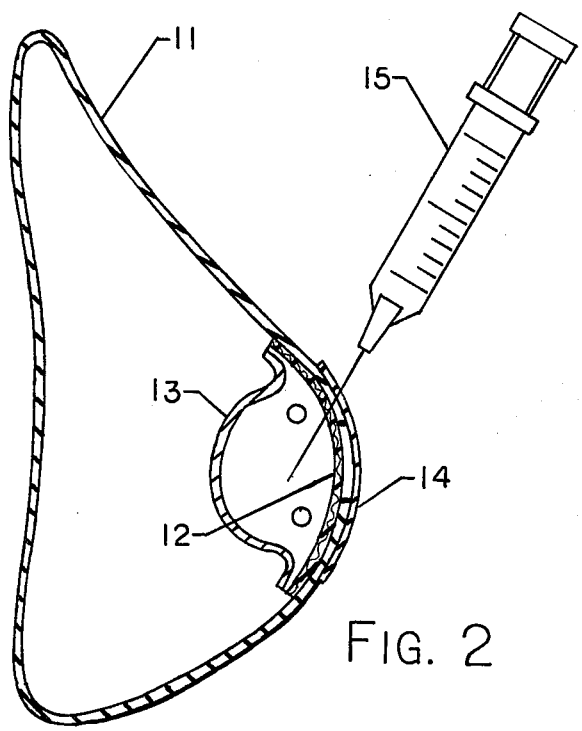
FIG. 2 is a cross-sectional view taken along the line 2—2 of FIG. 1 and showing use of the invention with a hypodermic syringe.

Referring now to the drawings wherein like reference characters designate like or corresponding parts throughout the figures thereof there is shown in FIGS. 1 and 2 an inflatable mammary prosthesis having an envelope 11 and an injection button 12 according to the present invention affixed to a portion of the envelope. As may be seen more clearly from FIG. 3, a patch 14 overlies the hole in the envelope 11 which is utilized to place the injection button on the inside of the envelope.

Figure 3:
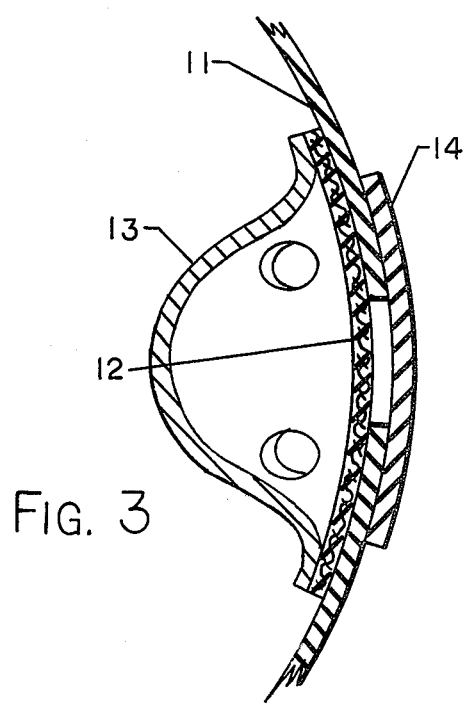
FIG. 3 is a fragmentary cross-sectional view of the injection area of the prosthesis shown in FIG. 2.

As shown in FIGS. 2 and 3, a needle guard 13 is secured to the envelope 11 at a position on its interior wall underlying the injection button 12 or to the underside of the injection button. The function of the injection button 12 may be seen in FIG. 2 in which a hypodermic needle 15 is shown in a position piercing the envelope and the button to inject fluid into the envelope or alternatively to remove fluid therefrom. The needle guard 13 serves to prevent accidental puncture of the back of the prosthesis envelope. The presence and shape of the needle guard, the placement of the injection button, and the precise type and shape of the prosthesis are immaterial to the invention and are chosen merely for illustrative purposes.

While the invention is shown for illustrative purposes in conjuction with an inflatable mammary prosthesis it is to be understood that the invention can be used in any application wherein it is desirable to introduce or remove fluids by means such as a hypodermic needle. Such applications include, for example, skin expanders, drug infusion devices, and inflatable restriction devices such as blood vessel restricters, all of which form no part of the present invention.

Figure 4:
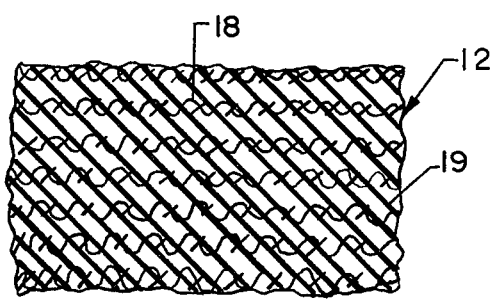
FIG. 4 is a further fragmentary view illustrating detail of the injection button shown in FIGS. 2 and 3.

Fuller appreciation of the details and function of the injection button of the present invention will become apparent from a description of its preferred method of manufacture and from FIG. 3 of the drawings which shows a fragmentary view of the injection button and prosthesis and FIG. 4 which shows a greatly enlarged cross-section of a portion of an injection button per se showing the silicone rubber 19 and the fabric layers 18.

In its preferred embodiment the manufacturing method requires sheeted uncured silicone rubber stock and sheets of reinforcing fabric which is preferably a woven open mesh polyester. The silicone rubber stock may be any of the conventional heat curable medical grade dimethylpolysiloxane based stocks suitable for implantation in the body. The fabric chosen should be relative nonstretchable in at least one direction. The rubber stock sheeting must have a thickness sufficient to allow total embedment of the fabric in the rubber stock, and therefore must have a thickness at least equal to the thickness of the fabric unless multiple sheets are used as in effect a single sheet.

In a specific embodiment 8 sheets of Dacron polyester fabric sold under the designation 6116 by Travis Mills Corporation and which has a thickness of 0.006 inch are used with seven layers of 0.008 inch thick non-reinforced uncured silicone rubber sheeting, which may if desired incorporate a radioopaque pigment. The Dacron 6116 fabric is woven from 40 denier monofilament polyester sold by E. I. duPont deNemours and Co. under the designation Dacron type 52. A composite structure is made by interleaving the uncured rubber sheets between the fabric sheets. Because the Dacron 6116 has a directional weave and is stretchable in one direction, multiple sheets are used and the fabric sheets are rotated relative to one another as the composite structure is being laid up to provide substantially uniform stretch characteristics in all directions.

Figure 6:
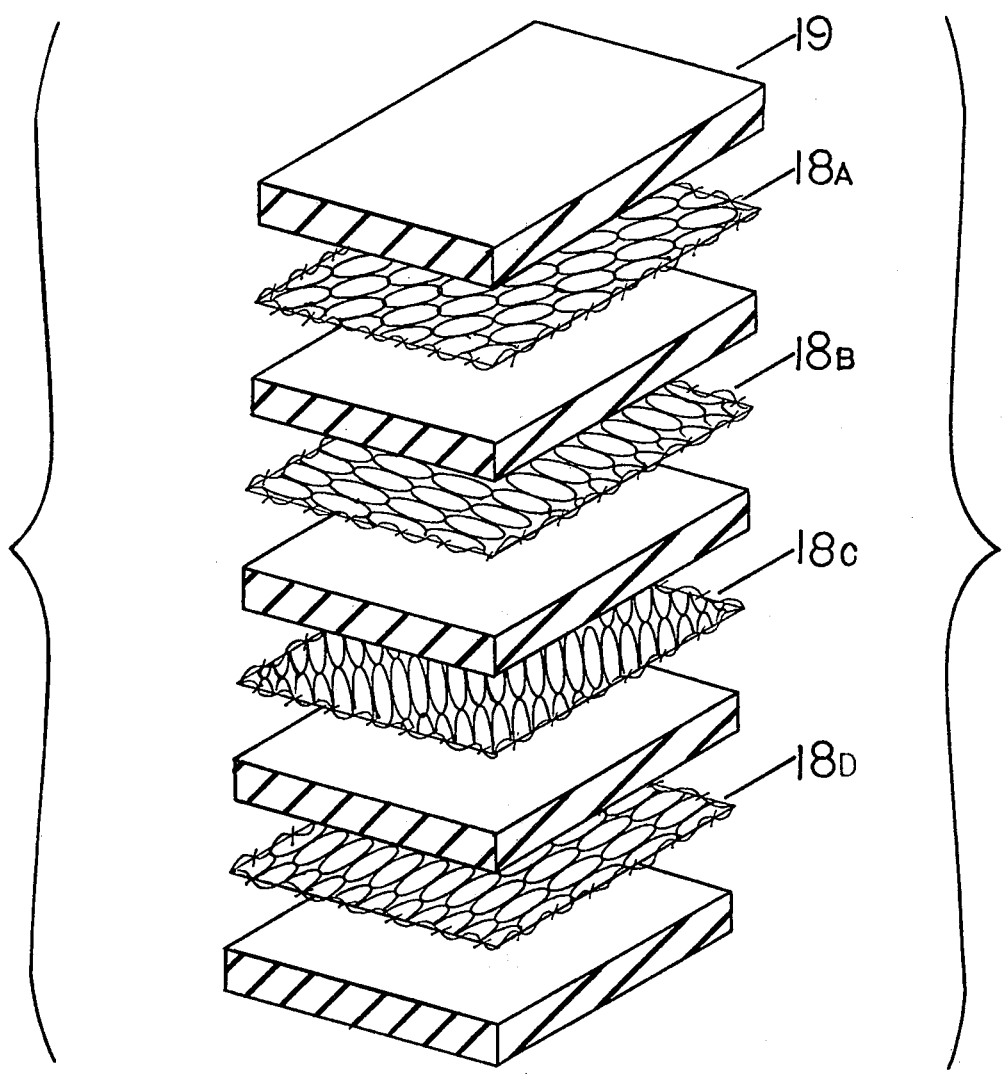
FIG. 6 is an exploded, partially schematic view of FIG. 4 showing interleaving alternate sheets of silicone rubber and fabric.

FIG. 6 is an exploded, partially schematic view of FIG. 4 showing a plurality of interleaving alternate sheets of silicone rubber 19 and fabric 18 to illustrate the above specific embodiment. Only four fabric sheets, instead of eight, are shown for the purposes of clarity. Furthermore, FIG. 6 illustrates the use of multiple parallel layers of fabric where the fabric sheets have a directional weave and the adjacent fabric sheets 18A, 18B, 18C and 18D are oriented in more than one weave direction.

The resulting laid up composite is placed in a chase and pressed and cured for ten minutes at 300° F. the composite has the cloth fabric completely embedded in partially cured silicone rubber. The composite is then placed in an oven to cure four hours at 350° F. The cured composite is then preferably die cut into the shapes of the desired injection buttons. The die cutting exposes uncoated ends of the fabric.

The cut composite is immersed in a swelling agent to cause swelling of the rubber. While silicone rubber can be swollen with a number of liquids a very suitable swelling medium for medical applications is dimethylpolysiloxane fluid. The swelling agent must be nonvolatile under atmospheric conditions if the device is to be stored for any length of time and must for medical use be biologically compatible. Polydimethylsiloxane fluid of 100 Cs viscosity is sufficiently nonvolatile and biologically compatible to serve the purpose. The cut ends of the fabric in the cured composite serve to help wick fluid into the material and a two week immersion has been found satisfactory. The fluid may be washed from the surfaces with solvent prior to applying adhesive to affix the injection button in place on the device on which it is to be used. Isopropanol is a suitable solvent for this purpose.

As may be seen from FIG. 4, the injection button formed as described above is a composite of swollen silicone rubber and fabric. The swollen rubber, however, is under substantial compressive stress by virtue of its being held in place to large a degree by the fabric interstices. Due to the fact that the total composite is substantially nonstretchable in any direction by virtue of the rotated fabric layers, no substantial stress relief is inherent in the system. The device is designed to be punctured in use by means such as a hypodermic needle and when the needle is withdrawn the internal stresses serve to close the void instantly.

Figure 5:
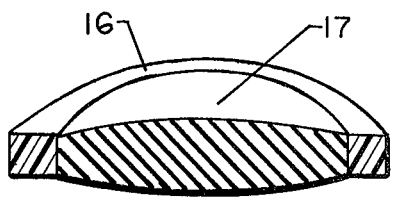
FIG. 5 is a perspective view, partly in cross-section, of another embodiment of the invention.

While the preferred embodiment utilizes multiple sheets of relatively thin polyester fabric in the composite it is to be understood that single sheets of cloth or metal fabric such as stainless steel can be used as long as the material is sufficiently rigid to maintain a degree of compression in swollen rubber. As illustrated in FIG. 5, a similar result can be obtained by using a rigid metallic or plastic ring 16 as the retention means for holding the rubber 17 in compression. In such instance uncured rubber is molded into the ring 16 and cured. The composite is then immersed in a swelling agent as heretofore described with respect to the embodiment of FIGS. 1–4. This embodiment however suffers from bulkiness and a more uneven compression distribution in the button.

Other embodiments will become apparent to those skilled in the art from a reading of the foregoing. It is to be understood therefore that within the scope of the appended claims the invention may be practiced otherwise than as specifically described.

That which is claimed is:

1. A self-sealing injection button adapted to be pierced by a hypodermic needle, said injection button comprising a unitary body of cured silicone rubber swollen with a swelling agent which is nonvolatile under atmospheric conditions, and a restraining means for preventing the swollen silicone rubber from occupying the volume it would ordinarily occupy in the absence of the restraining means to provide and maintain compressive forces within the silicone rubber for sealing punctures, said restraining means comprising multiple parallel layers of fabric oriented in more than one weave direction, said layers being impregnated with and in intimate contact with the silicone rubber.

2. A self-sealing injection button adapted to be pierced by a hypodermic needle, said injection button comprising a unitary body of cured silicone rubber swollen with a swelling agent, and restraining means for holding said rubber to provide compressive forces therein for sealing punctures wherein said restraining means is a retention means in the form of a rigid ring surrounding the silicone rubber.

3. A self-sealing injection button as defined in claim 2 wherein said swelling agent is nonvolatile under atmospheric conditions and the swelling agent is dimethylpolysiloxane fluid.

4. A self-sealing injection button adapted to be pierced by a hypodermic needle, said injection button comprising a unitary body of cured silicone rubber swollen with a swelling agent, and restraining means for holding said rubber to provide compressive forces therein for sealing punctures wherein the restraining means comprise at least one sheet of fabric which is impregnated with said rubber, said restraining means including multiple parallel layers of fabric wherein said layers of fabric are oriented in more than one weave direction.

5. A method of making a self-sealing injection button adapted to be pierced by a hypodermic needle, said method comprising interleaving alternate sheets of uncured silicone rubber and at least one sheet of fabric to form a composite, applying pressure to the composite to embed the fabric sheets in the uncured rubber, curing the silicone rubber in the composite, and swelling the cured silicone rubber by immersing it in a swelling agent to thereby provide internal compressive forces within the composite.

6. A method of making a self-sealing injection button as set forth in claim 5 wherein adjacent layers of fabric are oriented in different weave directions as said composite is formed.

7. A method of making a self-sealing injection button as defined in claim 6 wherein said swelling agent is nonvolatile under atmospheric conditions.

8. A method of making a self-sealing injection button as defined in claim 7 wherein said swelling agent is polydimethylsiloxane fluid.

9. A method of making a self-sealing injection button as defined in claim 8 which further includes, prior to swelling the cured silicone rubber, cutting the cured composite to expose edge portions of the fabric to thereby enhance absorption of fluid during swelling.

* * * * *